United States Patent [19]

Schwarz

[11] Patent Number: 4,659,826

[45] Date of Patent: Apr. 21, 1987

[54] SYNTHESIS OF SALICYLAMIDES WITH IMPROVED YIELD AND PURITY

[75] Inventor: Joshua Schwarz, Brooklyn, N.Y.

[73] Assignee: Lever Brothers Company, New York, N.Y.

[21] Appl. No.: 673,307

[22] Filed: Nov. 20, 1984

Related U.S. Application Data

[63] Continuation-in-part of Ser. No. 555,760, Nov. 28, 1983, abandoned.

[51] Int. Cl.$^4$ .......................................... C07C 103/22
[52] U.S. Cl. ..................... 544/277; 548/179; 548/195; 549/480; 564/134; 564/139; 564/169; 564/179
[58] Field of Search ............: 564/134, 139, 169, 179; 544/277; 548/179, 195; 549/480

[56] References Cited

U.S. PATENT DOCUMENTS

| | | | |
|---|---|---|---|
| 2,773,096 | 12/1956 | Sahyun | 564/134 |
| 3,244,520 | 4/1966 | Schulte | 564/134 |
| 3,907,893 | 9/1975 | Parker | 260/562 R |
| 4,287,191 | 9/1981 | Coburn et al. | 564/169 |
| 4,358,443 | 11/1982 | Coburn et al. | 564/169 |

FOREIGN PATENT DOCUMENTS

| | | | |
|---|---|---|---|
| 241990 | 1/1960 | Australia . | |
| 590180 | 1/1960 | Canada | 564/179 |
| 105606 | 6/1966 | India . | |

OTHER PUBLICATIONS

March, Jerry, "Advanced Organic Chemistry", McGraw Hill Book Company, 1977, pp. 386 & 387.
J. Van Allan and C. F. H. Allen, "Organic Syntheses Collective vol. 3", pp. 765-767 (1946).
VanAllan, J. A., "Journal of the American Chemical Society", 69, 2913 (1947).
Kirby, A. J. et al., "Journal of the Chemical Society", Perkin Transactions II (1979) p. 1610.
Fife, T. H. et al., "Journal of the American Chemical Society", 105 74 (1983).
Advanced Organic Chemistry, Second Edition, by Jerry March, p. 806, McGraw Hill Book Co.
The Chemistry of Imines by Robert W. Layer, p. 497, Chemical Reviews 63, 1963.

*Primary Examiner*—Robert J. Warden
*Assistant Examiner*—Robert Benson
*Attorney, Agent, or Firm*—Gerard J. McGowan, Jr.; James J. Farrell

[57] ABSTRACT

A method of synthesizing and recovering with high yield and purity salicylamide compounds of the formula:

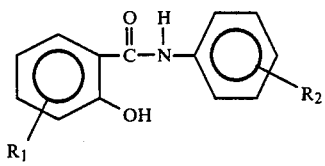

or

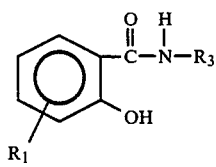

wherein $R_1$ is a substituent having the formula $-COC_nH_{2n+1}$ wherein n is an integer with a value of from 1 through to about 15, $R_2$ is a substituent selected from the group consisting of $-H$, $-NO_2$, $-F$, $-Cl$, $-Br$, $-I$, $-CF_3$, $-CBr_3$, $-CCl_3$, $-CI_3$ and $R_1$ and $R_3$ is an $R_2$ substituted heterocyclic compound selected (e.g.) from the group consisting of furan, thiazole, benzothiazole and purine by:

(a) reacting a phenyl salicylate ester bearing an $R_1$ substituent on the benzene ring of the salicylic acid portion thereof with an $R_2$ substituted aniline or a heterocyclic amine $NH_2$-$R_3$, optionally in the presence of an inert solvent such as a halogenated or unhalogenated aromatic compound or a carbowax solvent, e.g., a polyethylene glycol of average molecular weight 1000 to 6000 or mixtures thereof at a temperature of above about 150° C. for about 2 to about 6 hours to form a reaction mixture;

(b) dissolving the reaction mixture in a solvent to form a dissolved reaction mixture;

(c) acidifying the dissolved reaction mixture with an aqueous solution of a Lowry-Bronsted acid to form an acidified dissolved reaction mixture;

(d) refluxing the acidified dissolved reaction mixture to produce a final reaction mixture;

(e) adding water to the final reaction mixture to precipitate the product salicylamide compound; and (f) recovering the precipitated product salicylamide compound from the final reaction mixture.

19 Claims, No Drawings

SYNTHESIS OF SALICYLAMIDES WITH IMPROVED YIELD AND PURITY

This is a continuation-in-part of Ser. No. 555,760 filed 11/28/83, now abandoned.

This invention relates to a new and improved process for the preparation of substituted salicylamides in high yield and purity from substituted phenyl salicylates and substituted anilines or heterocyclic amines.

Salicylamide compounds, especially those bearing n-alkyl or n-alkanoyl substituents in the benzene ring of the salicylic acid portion thereof have numerous uses. U.S. Pat. Nos. 4,358,443 and 4,287,191 teach the use of such compounds as bactericides and as anti-dental plaque agents. Commonly assigned U.S. patent application No. 525,916 (hereinafter referred to as Ritchey) filed on Aug. 24, 1983 teaches the use of a wide variety of salicylamide compounds as (inter alia) anti-inflammatory and analgesic agents. The disclosure of Ritchey is hereby incorporated by reference in its entirety.

The invention particularly pertains to a new and improved process for the synthesis of substituted salicylamides wherein a substituted phenyl salicylate is reacted with an excess quantity of a substituted aniline or a substituted heterocyclic amine in a neat melt or in the presence of a diluent which does not interfere with the formation of the substituted salicylamide products. Thereafter, a new and improved purification procedure enables the recovery of the substituted salicylamide product in greatly enhanced yields and purity.

The synthesis of a typical unsubstituted salicylamide is conventionally conducted by the reaction of salicylic acid and aniline in the presence of phosphorus trichloride as a condensing agent. U.S. Pat. Nos. 2,763,683; 3,221,051; 3,221,052; and 3,231,611 describe various processes for the preparation and purification of salicylanilide. However, while the processes described therein are presumably quite effective for the preparation and purification of the parent salicylanilide, they are not practical for the preparation of salicylanilides substituted in the salicyl and/or aniline portions of the molecule or other salicylamide compounds wherein the aniline portion of the molecule is wholly replaced by a substituted or unsubstituted heterocyclic amine.

Ritchey describes the synthesis of salicylamide compounds by the reaction of 5-acyl or 5-alkyl salicylic acid with a substituted aniline in a reaction solvent such as chlorobenzene in the presence of phosphorus trichloride adopting the teachings of U.S. Pat. No. 4,287,191 in that regard.

There is another somewhat more cumbersome method for the preparation of salicylamindes known as the salol reaction. Salol is a common name for phenyl salicylate and the salol process involves the formation of amides of salicylic acid by the heating of phenyl salicylate with an amine which may be an aniline or a heterocyclic amine. The earliest report relative to the salol process appears to be by M. Schopff, Ber. 25, 2740 (1892). A concise description of the salol process in the English language is contained in the Merck Index, 8th Edition, page 1211 together with a listing of various other publications in which the salol reaction has been mentioned or discussed.

According to the salol process, a given quantity of phenyl salicylate is heated with at least a stoichiometric corresponding quantity of aniline, usually in a high boiling aromatic diluent at temperatures approaching and even exceeding 200° C. for several hours. The resulting reaction product is thereafter allowed to crystallize, washed with ligroin and optionally recrystallized from ethanol. The aforementioned process has been described with reference to the preparation of both the parent salicylanilide as well as several salicylanilides where the substitution has been in the benzene ring of the aniline portion alone.

According to a report by C. F. H. Allen, et al. in "Organic Syntheses, Collective Volume III", 765 (1955), when the parent salicylanilide compound is synthesized the yield is only about 70% and moreover, the resulting product has a persistent pink color which is not easily removed. While Allen, et al. do report higher yields in the syntheses of other salicylamides, it is interesting to note that the only variation from the basic salol process synthesis of salicylanilide suggested therein is one involving the use of different anilines and heterocyclic amines. There is no suggestion made therein with respect to the utility or otherwise of the salol process in those cases where the phenyl salicylate reactant itself incorporates a substituent or substituents upon its salicylic acid benzene ring.

Due consideration of mechanistic concepts enables one to conclude that substitution of the benzene ring of the salicylic acid portion of the phenyl salicylate molecule with an alkyl and especially an alkanoyl group would lead to considerable more complexity in the reaction pathway as a result of the complexation of the aniline or other amine with the alkyl or alkanoyl substituent group. The result would be lower yields of the desired product, increased side reactions and more difficulty in purifying the desired salicylamide product.

Accordingly, this invention relates to a new and improved process for the preparation of salicylanilides of the type

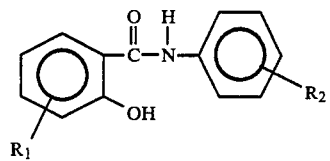

wherein $R_1 = -COC_nH_{2n+1}$, wherein n is an integer with a value of from 1 through to about 15 and $R_2 = -H, -NO_2, -F, -Cl, -Br, -I, -CF_3, -CBr_3, -CCl_3, -CI_3$ and (other groups) from substituted or unsubstituted phenyl salicylates and substituted or unsubstituted anilines. $R_2$ will generally be an electron withdrawing group although it may also be electron donating in which case it may, optionally, be identical with $R_1$. The term "anilines" as used herein is intended to embrace aromatic amines in general, whether they are heterocyclic or not.

Accordingly, in another embodiment of this invention, the inventive process relates to the preparation of a salicylamide of the formula shown below:

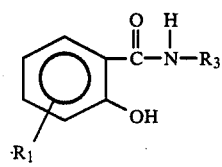

wherein $R_1$ has the meaning already ascribed to it above and $R_3$ is a heterocyclic aromatic group with or without the same substituents as those represented by $R_2$. Non-limiting examples of heterocyclic amines which are suitable for the practice of this invention include 2-aminofuran, 2-aminothiazole and 2-aminobenzothiazole and 8-aminopurine.

As will also be readily apparent to persons of ordinary skill in the art to which the invention pertains, the aromatic amine reactants employed within the practice of the invention (whether or not they are heterocyclic) may be primary or secondary. When the reactant amine is primary, the resulting product will be a secondary salicylamide. When the reactant amine is secondary, the resulting product will be a tertiary salicylamide.

As will be readily apparent to a person of ordinary skill in the art to which the invention pertains, any of the large number of salicylamide compounds disclosed by Ritchey may by synthesized pursuant to the procedure disclosed and claimed herein provided only that the substituents taught by Ritchey (whether they be upon the salicylic acid benzene ring or upon the aniline or heterocyclic amine ring of the respective salicylamide compounds) do not interfere with the overall reaction and purification schemes of this invention. Again, a person of ordinary skill in the art to which the invention pertains will be able to determine with routine non-inventive experimentation which one of the substituents disclosed by Ritchey will or will not interfere with the reaction scheme of the present invention.

According to this invention, a method is provided for the synthesis and recovery with high yield and purity of salicylamide compounds which comprises the steps of:

(a) reacting about one mole part of a phenyl salicylate ester bearing an $R_1$ substituent on the benzene ring of the salicylic acid portion thereof with about one to two mole parts of an $R_1$ or $R_2$ substituted aniline or a heterocyclic amine $NH_2$—$R_3$. A mole ratio of the aniline or amine to ester of about 1 to 1 to 1.5 to 1 or more preferably about 1.2 to 1 to 1.3 to 1. The mole ratio selected is based mainly on economics. The most expensive reactant is the salicylate ester and, accordingly, it is desired to use a sufficient excess of the amine or aniline reactant to react completely with the ester. When $R_1$ is —$COC_nH_{2n+1}$, however, large excesses of the amine reactant are undesirable because of Schiff base side product formation by reaction of the amine with the carbonyl group of the side chain. The discovery of this side product formation led to refluxing the acidified reaction mixture in order to hydrolyze any Schiff base present and thereby recover additional desired product. The reaction may optionally be performed in the presence of an inert solvent system such as halogenated or unhalogenated aromatic compounds or a carbowax solvent, e.g., a polyethylene glycol of average molecular weight about 1000 to about 6000 or mixtures thereof all having a melting point of up to 120° C. The reaction is performed at a temperature of between about 150° C. to about 225° C. for about 2 to about 6 hours to form a reaction mixture;

(b) dissolving the reaction mixture in a polar organic solvent such as alkanols, halogenated hydrocarbons and mixtures thereof all having a boiling point of up to about 200° C. (e.g., ethanol or methylene chloride) after optional cooling to a temperature of about 120° C. to about 40° C. to form a dissolved reaction mixture;

(c) acidifying the dissolved reaction mixture with an aqueous solutin of a Lowry-Bronsted acid (e.g., hydrochloric acid) to form an acidified dissolved reaction mixture;

(d) refluxing the acidified dissolved reaction mixture at a sufficiently high temperature to form the product for a few minutes up to about one hour or even longer to produce a final reaction mixture. Longer times may be used but could result in undesirable hydrolysis of the product. Preferably, reflux will be from about 15 to 30 minutes to minimize undesirable hydrolysis. The reflux temperature can vary widely depending on the solvent used, e.g., methanol, ethanol, isopropanol, n-propanol, and the like. When ethanol is used, the mixture refluxes at about 80° C. It is possible to use temperatures between about 40° C. and 120° C. or even higher if the reflux were operated under pressure. The lower the temperature the longer the heating time required while higher temperatures require shorter heating times compared to the fifteen minutes preferably used when the temperature is 80° C.;

(e) adding water to the final reaction mixture to precipitate the product salicylamide compound; and (f) recovering the precipitated product salicylamide compound from the final reaction mixture.

Thereafter, the product salicylamide compound may, if desired, be purified by recrystallization from (e.g.) isopropanol, ethanol or an ethanol/water mixture. Any other solvent in which the product salicylamide dissolves may be gainfully employed for the foregoing purpose. The choice of a suitable solvent will be a matter of obvious alternatives to a person of ordinary skill in the art to which the invention relates.

The following Examples which are submitted for illustrative purposes only demonstrate the particular utility of synthesizing a representative salicylamide compound, i.e., 3'-trifluoromethyl-5-octanoylsalicylanilide with remarkably high yields and exceptionally high purity. The purity of the salicylamide reaction product was determined in each case using high performance liquid chromatography, as well as standard spectroscopic methods, including nuclear magnetic resonance spectral analyses.

EXAMPLE 1

50 g (0.147 mole) 5-octanoyl phenyl salicylate and 29.6 g (0.184 mole) 3-aminobenzotrifluoride, also known as metatrifluoromethylaniline, were placed in a reaction vessel under a blanket of nitrogen. The mixture was heated to 180° for 3.5 hours. The temperature was lowered to about 100° C. and about 80 ml of ethanol was added to dissolve the reaction mixture. About 10 ml of concentrated hydrochloric acid (37%) was added to 10 ml of water and then added slowly to the reaction vessel with vigorous stirring. The reaction mixture was refluxed at about 80° C. for about 15 minutes. 25 ml of water was then added with vigorous stirring whereupon a yellow solid product precipitated out. After drying, the solid product was stirred with about 225 ml petroleum ether and filtered. This resulted in 42.5 g of the product, i.e., 3'-trifluoromethyl-5-octanoyl-salicylanilide. The product was dissolved in sufficient ethanol to effect dissolution and water was thereafter dropwise added to the cloud point of the solution. Thereafter, the purified product was precipitated by cooling the solution. Recrystallization as aforesaid from said ethanol/water mixture yielded 38.2 g (0.113 mole) of product with purity greater than 99.5%.

It will be noted that the product yield obtained was 76.9% upon the basis of the 5-octanoyl phenyl salicylate reactant.

EXAMPLE 2

50 g (0.147 mole) of 5-octanoyl phenyl salicylate and 29.8 g (0.185 mole) of 3-aminobenzotrifluoride were placed in a reaction vessel under a blanket of nitrogen. The mixture was heated to 150°–155° C. for 6 hours. The temperature was lowered to about 100° C. and about 80 ml of ethanol was added to dissolve the reaction mixture. About 10 ml of concentrated hydrochloric acid (37%) was added to 10 ml of water and then added slowly to the reaction vessel with vigorous stirring. The reaction mixture was refluxed at about 80° C. for about 15 minutes. 25 ml of water was then added with vigorous stirring whereupon a yellow solid product precipitated out. The solid product was recovered by filtration and washed with water. After drying, the solid product was stirred with about 225 ml petroleum ether and again filtered. This resulted in 41.9 g (0.103 mole) of the product, i.e., 3'-trifluoromethyl-5-octanoylsalicylanilide. Recrystallization from an ethanol/water mixture in accordance with the procedure of Example 1 yielded 35.9 g (0.088 mole) of product with purity greater than 99.5%.

It will be noted that the initial product yield obtained was 70.1% upon the basis of the 5-octanoyl phenyl salicylate reactant. In this particular case, it will also be noted that the net yield of the product salicylamide was 59.9% upon the basis of the precursor 5-octanoyl phenyl salicylate following the recrystallization of the initially obtained product from an ethanol/water mixture.

EXAMPLE 3

50 g (0.147 mole) of 5-octanoyl phenyl salicylate and 29.8 g (0.185 mole) of 3-aminobenzotrifluoride were placed in a reaction vessel under a blanket of nitrogen. The mixture was heated to 200°–205° C. for 2 hours. The temperature was lowered to about 100° C. and about 80 ml of ethanol was added to dissolve the reaction mixture. About 10 ml of concentrated hydrochloric acid (37%) was added to 10 ml of water and then added slowly to the reaction vessel with vigorous stirring. The reaction mixture was refluxed at about 80° C. for about 15 minutes. 25 ml of water was then added with vigorous stirring whereupon a yellow solid product precipitated out. The solid product was recovered by filtration and washed with water. After drying, the solid product was stirred with about 225 ml petroleum ether and again filtered. This resulted in 42.5 g of the product, i.e., 3'-trifluoromethyl-5-octanoylsalicylanilide. Recrystallization from an ethanol/water mixture in accordance with the procedure of Example 1 yielded 38.2 g (0.113 mole) of product with purity greater than 99.5%.

It will be noted that the product yield obtained was 76.9% upon the basis of the 5-octanoyl phenyl salicylate reactant.

EXAMPLE 4

20 g (0.058 mole) of 5-octanoyl phenyl salicylanilide and 11.9 g (0.073 mole) of 3-aminobenzotrifluoride were placed in reaction vessel with 45 ml of 1,2,4-trichlorobenzene under a blanket of nitrogen. The mixture was heated to 225° C. for 4 hours. It was then allowed to cool to about 40° C. at which time 20 ml of methylene chloride was added to avoid solidification of the reaction mixture. Upon further cooling in an ice-water bath, a yellow solid product precipitated out and was recovered by filtration. About 5 ml of concentrated hydrochloric acid (37%) was added to 5 ml of water and 30 ml of ethanol in a flask. The yellow solid product was added to the flask with vigorous stirring and the dissolved mixture was refluxed at about 80° C. for about 15 minutes. 15 ml of water was then added thereto with vigorous stirring whereupon a slightly yellowish solid precipitated out. The precipitate was recovered by filtration, dried and recrystallized from ethanol to yield 17 g (0.042 mole) of the pure product, i.e., 3'-trifluoromethyl-5-octanoylsalicylanilide.

It will be noted that the product yield obtained was 72.4% upon the basis of the 5-octanoyl phenyl salicylate reactant.

The invention is further defined by and should be read in conjunction with the appended claims.

What is claimed is:

1. A method of synthesizing and recovering with high yield and purity salicylamide compounds of the formula:

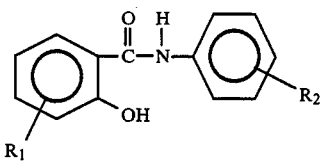

wherein $R_1$ is a substituent having the formula, $-COC_nH_{2n+1}$ wherein n is an integer with a value of from 1 through to about 15 and $R_2$ is a substituent selected from the group consisting of $-H$, $-NO_2$, $-F$, $-Cl$, $-Br$, $-I$, $-CF_3$, $-CBr_3$, $-CCl_3$, $-CI_3$ and $R_1$ which comprises the steps of:

(a) heating a phenyl salicylate ester bearing an $R_1$ substituent on the benzene ring of the salicylic acid portion thereof with an $R_2$ substituted aniline in a mole ratio of said ester to said substituted aniline of about one to one to one to two at a temperature of above about 150° C. for about 2 to about 6 hours to form a reaction mixture;

(b) dissolving the reaction mixture in a solvent selected from the group consisting of polar organic solvents, non-polar halogenated hydrocarbons and mixtures thereof to form a dissolved reaction mixture;

(c) acidifying the dissolved reaction mixture with an aqueous solution of a Lowry-Bronsted acid to form an acidified dissolved reaction mixture;

(d) refluxing the acidified dissolved reaction mixture to produce a final reaction mixture;

(e) adding water to the final reaction mixture to precipitate the product salicylamide compound; and (f) recovering the precipitated product salicylamide compound from the final reaction mixture.

2. The method of claim 1 wherein the phenyl salicylate ester and the aniline are reacted at a temperature in the range of about 150° C. to about 225° C.

3. The method of claim 1 wherein the reaction mixture is cooled to a temperature in the range of about 120° C. to about 40° C. prior to the addition of said solvent.

4. The method of claim 1 wherein said solvent is selected from the group consisting of alkanols having a boiling point of up to 200° C., halogenated alkanes having a boiling point of up to 200° C. and mixtures thereof.

5. The method of claim 1 wherein the Lowry-Bronsted acid is hydrochloric acid.

6. A method according to claim 1 wherein the phenylsalicylate ester and the aniline are reacted in the presence of an organic solvent system selected from the group consisting of halogenated aromatic compounds having a melting point of up to 120° C., unhalogenated aromatic compounds having a melting point of up to 120° C., polyethylene glycols having an average molecular weight of about 1000 to about 6000 and mixtures thereof.

7. A method for synthesizing and recovering with high yield and purity salicylamide compounds of the formula:

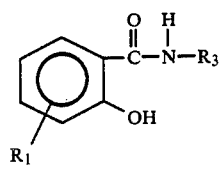

wherein $R_1$ is a substituent having the formula —$COC_nH_{2n+1}$ wherein n is an integer with a value of from 1 through to about 15 and $R_3$ is a monocyclic or polycyclic aromatic or heteroaromatic group, wherein the polycyclic group can be fused or nonfused, either unsubstituted or bearing substituents thereon selected from the group consisting of —$NO_2$, —F, —Cl, —Br, —I, —$CF_3$, —$CBr_3$, —$CCl_3$ and $R_1$ which comprises the steps of:

(a) heating a phenyl salicylate ester bearing an $R_1$ substituent on the benzene ring of the salicylic acid portion thereof with an amine $NH_2$—$R_3$ in a mole ratio of said ester to said amine of about one to one to one to two at a temperature of above about 150° C. for about two to about six hours to form a reaction mixture;

(b) dissolving the reaction mixture in a solvent selected from the group consisting of polar organic solvents, non-polar halogenated hydrocarbons and mixtures thereof to form a dissolved reaction mixture;

(c) acidifying the dissolved reaction mixture with an aqueous solution of a Lowry-Bronsted acid to form an acidified dissolved reaction mixture;

(d) refluxing the acidified dissolved reaction mixture to produce a final reaction mixture;

(e) adding water to the final reaction mixture to precipitate the product salicylamide compound; and (f) recovering the precipitated product salicylamide compound from the final reaction mixture.

8. The method of claim 7 wherein the phenyl salicylate ester and the heterocyclic amine are reacted at a temperature in the range of about 150° C. to about 225° C.

9. The method of claim 7 wherein the reaction mixture is cooled to a temperature in the range of about 120° C. to about 40° C. prior to the addition of said polar organic solvent.

10. The method of claim 7 wherein said solvent is selected from the group consisting of alkanols having a boiling point of up to 200° C., halogenated alkanes having a boiling point of up to 200° C. and mixtures thereof.

11. The method of claim 7 wherein the Lowry-Bronsted acid is a hydrochloric acid.

12. The method of claim 7 wherein the heterocyclic aromatic group $R_3$ is one selected from the group consisting of furan, thiazole, benzothiazole and purine.

13. The method of claim 7 wherein the phenyl salicylate ester and the heterocyclic amine are reacted in the presence of an organic solvent system selected from the group consisting of halogenated aromatic compounds having a melting point of up to 120° C., unhalogenated aromatic compounds having a melting point of up to 120° C., polyethylene glycols having an average molecular weight of about 1000 to about 6000 and mixtures thereof.

14. The method of claim 1 wherein step (d), refluxing the acidified dissolved reaction mixture to produce a final reaction mixture, is carried out for three minutes to one hour.

15. The method of claim 1 wherein step (d), refluxing the acidified dissolved reaction mixture to produce a final reaction mixture, is carried out for fifteen to thirty minutes.

16. The method of claim 7 wherein step (d), refluxing the acidified dissolved reaction mixture to produce a final reaction mixture, is carried out for three minutes to one hour.

17. The method of claim 7 wherein step (d), refluxing the acidified dissolved reaction mixture to produce a final reaction mixture, is carried out for fifteen to thirty minutes.

18. Process according to claim 1 wherein $R_2$ is selected from the group consisting of —$CF_3$, —$CBr_3$, and —$CCl_3$.

19. Process according to claim 18 wherein $R_2$ is $CF_3$ in the 3 position.

* * * * *